US012668608B2

(12) United States Patent
Youte Tendoung et al.

(10) Patent No.: US 12,668,608 B2
(45) Date of Patent: Jun. 30, 2026

(54) METHOD FOR SYNTHESIZING MACROMOLECULES IN SOLUTION FROM CARBOHYDRATE DERIVATIVE UNITS

(71) Applicant: STRAINCHEM, Saint-Beauzire (FR)

(72) Inventors: Jean-Jacques Youte Tendoung, Pont du Château (FR); Audrey Serre, Clermont-Ferrand (FR)

(73) Assignee: STRAINCHEM, Saint-Beauzire (FR)

( * ) Notice: Subject to any disclaimer, the term of this patent is extended or adjusted under 35 U.S.C. 154(b) by 586 days.

(21) Appl. No.: 18/012,253

(22) PCT Filed: Jun. 23, 2021

(86) PCT No.: PCT/IB2021/055523
§ 371 (c)(1),
(2) Date: Dec. 22, 2022

(87) PCT Pub. No.: WO2021/260562
PCT Pub. Date: Dec. 30, 2021

(65) Prior Publication Data

US 2023/0265119 A1 Aug. 24, 2023

(30) Foreign Application Priority Data

Jun. 24, 2020 (FR) ....................................... 2006615
Jun. 25, 2020 (FR) ....................................... 2006654

(51) Int. Cl.
*C07H 19/10* (2006.01)
*C07H 1/00* (2006.01)
*C07H 5/06* (2006.01)

(52) U.S. Cl.
CPC ............... *C07H 19/10* (2013.01); *C07H 1/00* (2013.01); *C07H 5/06* (2013.01)

(58) Field of Classification Search
CPC ........... C07H 1/00; C07H 19/10; C07H 21/00
See application file for complete search history.

(56) References Cited

FOREIGN PATENT DOCUMENTS

EP 2857412 A1 4/2015

OTHER PUBLICATIONS

Bonora et al., Nucleic Acids Research, 1993, 21(5), p. 1213-1217. (Year: 1993).*
Li et al., Tetrahedron, 2005, 61, p. 12081-12092. (Year: 2005).*
Kim et al., "Liquid-Phase RNA Synthesis by Using Alkyl-Chain-Soluble Support", Chemistry—A European Journal,vol. 19, No. 26, Jun. 24, 2013 (Jun. 24, 2013), p. 8615-8620.
Gravert et al., "Organic Synthesis on Soluble Polymer Supports: Liquid-Phase Methodologies Polymers in Liquid-Phase Synthesis 490 A. Properties of Soluble Polymer Supports 490 B. Methods of Separating Polymers from Reaction Mixtures", Aug. 28, 1996.
Takahashi et al, "AJIPHASE : A Highly Efficient Synthetic Method for One-Pot Peptide Elongation in the Solution Phase by an Fmoc Strategy", Angewandte Chemie International Edition, vol. 56, No. 27, Jun. 7, 2017 (Jun. 7, 2017), p. 7803-7807.
Kamlesh J et al, "Large scale, liquid phase oligonucleotide synthesis by alkyl H-phosphonate approach", Bioorganic & Medicinal Chemistry,,vol. 8, No. 2, May 26, 2017 (May 26, 2017), p. 337-342.
Schwenger et al, "Solution-Phase Synthesis of Branched Oligonucleotides with up to 32 Nucleotides and the Reversible Formation of Materials", European Journal of Organic Chemistry,vol. 2017, No. 39, Oct. 25, 2017 (Oct. 25, 2017), p. 5852-5864.
Donga et al, "A Novel Approach to Oligonucleotide Synthesis Using an Imidazolium Ion Tag as a Soluble Support", Journal of Organic Chemistry,vol. 71, No. 20, Sep. 2, 2006 (Sep. 2, 2006), p. 7907-7910.
International Search Report and Written Opinion received for PCT Application No. PCT/IB2021/055523, mailed on Oct. 7, 2021, 16 pages including 3 pages of English Translation.

* cited by examiner

*Primary Examiner* — Jonathan S Lau
(74) *Attorney, Agent, or Firm* — Gearhart Law LLC

(57) ABSTRACT

The invention relates to a method for synthesising macromolecules made up of units U that are mostly monosaccharides or monosaccharide derivatives, by successive elongation of a first unit U1 attached by a covalent bond to an anchor molecule soluble in organic solvents. The elongation takes place by coupling with a monomer or oligomer M having at least two functions. The method is characterised in that the anchor molecule comprises a polyolefin chain or a polyolefin oligomer or a polyalkene, with at least 5 monomer units, and preferably between 10 and 50 monomer units, the polyolefin chain preferably being a polyisobutene chain.

18 Claims, No Drawings

METHOD FOR SYNTHESIZING MACROMOLECULES IN SOLUTION FROM CARBOHYDRATE DERIVATIVE UNITS

The present application is a U.S. national phase application of a PCT Application No. PCT/IB2021/055523 filed on Jun. 23, 2021, which claims a priority to France Patent Application No. 2006615 filed in France on Jun. 24, 2020, and claims a priority to France Patent Application No. 2006654 filed in France on Jun. 25, 2020 a disclosure of which are incorporated in their entireties by reference herein.

TECHNICAL FIELD OF THE INVENTION

The present invention belongs to the field of organic macromolecule synthesis. More specifically, the present invention relates to a method for producing macromolecules of interest from monosaccharide or oligosaccharide units or derivatives of such units. This method takes place in liquid phase (solution) and uses anchor molecules soluble in organic medium and more particularly in apolar solvents. These anchor molecules (or liquid support) confer to the macromolecules (or intermediates) of interest, when they are bound thereto: transient protection of at least one chemical functional group and excellent solubility in apolar organic solvents and consequently, purifications by simple extraction or by filtration on silica. The macromolecules targeted can in particular be macromolecules of biological interest, such as oligonucleotides and oligosaccharides, and they can contain units which are not mono- or oligo-saccharides.

STATE OF THE ART

The present invention relates to a new method for synthesizing macromolecules comprising units of monosaccharides and/or oligosaccharides and/or derivatives thereof; these units may be or may comprise in particular pentoses or hexoses. Thus, and more particularly, the present invention relates to the synthesis of oligonucleotides (or derivatives thereof) and the synthesis of oligosaccharides (or derivatives thereof).

Usually, oligonucleotides are prepared, at the laboratory scale, by solid support synthesis, with automatons. Numerous efforts have been made to improve this equipment at the industrial stage for larger productions (>1 kilogram). However, since the end of the last century, therapeutic oligonucleotides have experienced a great expansion triggering a real interest for these molecular species. To date, more than 100 oligonucleotides are in clinical trials and eight drugs have been approved by the Food and Drug Administration (FDA) (see Y. S. Sanghvi, "*A Status Update for Modified Oligonucleotides for Chemotherapeutics Applications*," *Curr. Protoc. Nucleic Acid Chem.* 2011, 46:4.1.1-4.1.22.).

The first oligonucleotide approved was fomivirsen or Vitravene™ (see M. D. de Smet et al, "*Fomovirsen—a phosphorothioate oligonucleotide for the treatment of CMV retinitis*", *Ocul. Immunol. Inflamm.* 1999, 7, 189-198 and S. T. Cooke et al, "*RNA-Targeted Therapeutics,*" *Cell Metabolism,* 2018, 27, 714-739), an oligodeoxynucleotide consisting of 21 units linked by phosphorothioate linkages. It is used in the treatment of cytomegalovirus retinitis. Later, Macugen™ (pegaptanib sodium) and Kynamro™ (mipomersen sodium) were successively approved in 2004 and 2013, indicated for the treatment of neovascular (wet) form of age-related macular degeneration (AMD) and homozygous familial hypercholesterolemia, respectively (see Sanghvi and Schulte, *Curr. Opin. Drug Discovery Dev.* 2004, 6, 765).

So far, solid-phase oligonucleotide synthesis has routinely produced kilogram-scale oligonucleotides with good qualities (see Sanghvi, Y. S. (2019) "*Large-scale automated synthesis of therapeutic oligonucleotides: A status update*", published in S. Agrwal & M. J. Gait (Eds.) *Advances in nucleic acid therapeutic* (pp. 453-473)). Although many optimization efforts have been made, there is still room for improvement in oligonucleotide production methods. Liquid phase oligonucleotide synthesis is increasingly positioned as an efficient response to oligonucleotide production.

Regardless of the phase (solid (heterogeneous) or liquid (solution)) in which the reaction takes place, oligonucleotide synthesis boils down to the formation of phosphoric ester bonds between nucleosides in a defined order (see H. Lönneberg, "*Synthesis of oligonucleotides on a soluble support*," Beilstein J. Org. Chem., 2017, 13, 1368-1387 and A. Molina & Y. S. Sanghvi, "*Liquid-Phase Oligonucleotide Synthesis: Past, Present, and Future Predictions*," Current Protocols in Nucleic Acid Chemistry, 2019, 77 (1)). Often, liquid-phase oligonucleotide synthesis (deoxyribonucleic acid (DNA) or ribonucleic acid (RNA)) begins with the attachment of the anchor molecule to the 3' end of a nucleoside; elongation occurs from 3' to 5'. At this stage, the first cycle of synthesis begins with a nucleoside derivative phosphorylated in 3' position (phosphoramidite or H-phosphinate or phosphotriester), which will react with the alcohol in 5' position of the nucleoside anchored to a synthesis support.

Except for of the reacting alcohol, all other nucleophilic functional groups have to be protected beforehand. Thus, amines of the nucleic bases are preferably protected by acylation (benzoyl for cytosine and adenine, isobutyl for guanine) whereas alcohol functional groups of deoxyribose and ribose are respectively masked by trityl (dimethoxytrityl or monomethoxytrityl) ethers in the 5' position and/or by silyl (tert-butyldimethylsilyl or triisopropylsilyloxymethyl) ethers in the 2' position.

Depending on the nature of the phosphorylated nucleoside chosen, operating conditions of the coupling reaction are different. In the case of nucleoside phosphoramidites (see S. L. Beaucage & M. H. Caruthers, "*Deoxynucleoside Phosphoramidites—A new Class of Key Intermediates for Deoxypolynucleotide Synthesis*", Tetrahedron Letters, 1981, 22, 1859-1862) and nucleoside H-phosphonates, coupling reactions are followed by an oxidation reaction to yield the corresponding phosphotriesters. In the case of nucleoside phosphates, the corresponding phosphotriesters are obtained by esterifications with the preceding nucleoside (see C. B. Reese & Z. Pei-Zhuo, "*Phosphotriester Approach to the Synthesis of Oligonucleotides: A Reappraisal*," J. Chem. Soc, Perkin Trans. 1, 1993, 2291-2301, V. A. Efimov et al, "*Application of new catalytic phosphate protecting groups for the highly efficient phosphotriester oligonucleotide synthesis*", Nucleic Acids Res. 1986, 14, 6525-6540, G. van der Marel et al, "*A New Approach to the Synthesis of Phosphotriester Intermediates of Nucleosides and Nucleic Acids*," Tetrahedron Lett. 1981, 22, 3887-3890 and E. de Vroom et al, "*Use of a 1-hydroxybenzotriazole activated phosphorylating reagent towards the synthesis of short RNA fragments in solution*," Nucleic Acids Res. 1986, 14, 5885-5900).

Various anchor molecules have been described in the literature in connection with liquid phase oligonucleotide synthesis. Historically, foundation for oligonucleotide synthesis was laid by the work of Hayatsu and Khorana (see "*Deoxyribooligonucleotide Synthesis on a Polymer Support*", J. Am. Chem. Soc. 1966, 88, 13, 3182-3183). This approach inspired by the peptide synthesis methodology described by Merriefield, used a soluble polystyrene as an anchor molecule grafted (5'-O-monomethoxytrityl (MMTr)). However, this polystyrene becomes insoluble in organic solvents beyond three nucleotides, and as a result, product isolation becomes poor.

Other polymers have been studied, such as cellulose (Biochemistry 1968, 7, 8, 2809-2813) or polyvinyl alcohol (H. Schott et al., "*Liquid-Phase-Synthese von Oligothymidylphosphaten*", Die Makromolekulare Chemie, 1973, 173, 247-251). In both cases, during the incorporation of the first nucleoside into the support, a so-called capping reaction of the free (non-functionalized) hydroxyl groups is necessary in order to avoid presence of truncated oligonucleotides at the end of the synthesis.

In the 1990s, another class of polymers was widely studied as an anchor molecule: polyethylene glycol (or PEG). With this type of soluble supports, Bonora's group achieved gram-scale synthesis of oligonucleotides while dramatically reducing handling time (see "*HELP* (*High Efficiency Liquid Phase*) *new oligonucleotide synthesis on soluble polymeric support*," Nucleic Acids Research, 1990, 18, 3155-3159 and "*Large scale, liquid phase synthesis of oligonucleotides by the phosphoramidite approach*," Nucleic Acids Research, 1993, 21, 1213-1217).

More recently, Livingston's group has developed and used membranes for molecular separations by nanofiltration (see P. R. J. Gaffney et al, "*Liquid-Phase Synthesis of 2'-Methyl-RNA on a Homostar Support through Organic-Solvent Nanofiltration*", Chem. Eur. J., 2015, 21, 9535-9543 and J. F. Kim et al, "*Organic Solvent Nanofimltration* (*OSN*): *A New Technology Platform for Liquid-Phase Oligonucleotide Synthesis* (*LPOS*)", Org. Proc. Res. Dev., 2016, 20, 1439-1452). They facilitate and accelerate purification steps of growing oligonucleotides.

In a general way, the use of polyethylene glycols (PEGs) as an anchor matrix has several advantages such as: use of acetonitrile as a solvent; obtaining oligonucleotides having good purity; simplified purifications (at each step); possibility of achieving reasonable quantities of oligonucleotides; versatility at the level of coupling reactions (phosphoramidites, H-phosphonate (see K. J. Padiya et al, "*Large Scale, Liquid Phase Oligonucleotide Synthesis by Alkyl H-phosphonate Approach*", Bioorg. Med. Chem., 2000, 8, 337-342) and phosphates) and the decrease in the amount of monomers involved.

The main obstacles to the use of PEGs on an industrial scale are: large number of precipitation steps; excessive consumption of solvents and cost of nanofiltration membranes.

In 2017, the use of an adamantane derivative was described as an anchor molecule for liquid-phase oligonucleotide synthesis (A. Schwenger et al., "*Solution-Phase Synthesis of Branched Oligonucleotides with up to* 32 *Nucleotides and the Reversible Formation of Materials*", Eur. J. Org. Chem., 2017, 5852-5864). One advantage of this support is purification by simple extraction. The main drawback of this anchor molecule is its low E-factor (which expresses the desired waste-to-product mass ratio) because a large volume of solvent is required for the different extraction purification steps. The same research group described a tetrasubstituted adamantane derivative as an anchor molecule for liquid phase oligonucleotide synthesis. Again, the large volume of solvent required for purifications and the excess of phosphoramidite monomers hinder its industrial development.

In 2006, the first ion anchor molecule, in this case of the imidazolium type, was described (R. A. Donga et al., "*A Novel Approach to Oligonucleotide Synthesis Using an Imidazolium Ion Tag as a Soluble Support*", J. Org. Chem., 2006, 71, 7907-7910). The purification of the elongating oligonucleotide is done by precipitation and extraction. In an industrial vision, this liquid support is weighted by the large volume of solvent necessary for the purifications of the growing oligonucleotide.

Soluble β-cyclodextrin type anchor molecules, based on D-glucopyranose, have been shown to be effective for the synthesis of oligonucleotides in the liquid phase (A. Gimenez Molina et al., "*Acetylated and Methylated B-Cyclodextrins as Viable Soluble Supports for the Synthesis of Short 2'-Oligodeoxyribo-nucleotides in Solution*", Molecules, 2012, 17, 12102-12120). Advantages associated with these soluble supports are their cost and a decrease in the amount of monomers required for the coupling steps.

Weak points of these matrices lie in the purification method. Indeed, for each cycle, a purification by chromatography column is mandatory.

Another class of anchor molecules, consisting of functionalized pentaerythritol derivatives, was described. They were used for the synthesis of DNA (V. Kungurtsev et al., "*Solution-Phase Synthesis of Short Oligo-2'-deoxyribonucleotides by Using Clustered Nucleosides as a Soluble Support*", (Eur. J. Org. Chem., 2013, 6687-6693) and RNA (A. Gimenez Molina et al., "*Solution phase synthesis of short oligoribonucleotides on a precipitative tetrapodal support*", Beilstein J. Org. Chem., 2014, 10, 2279-2285 and Current Organic Synthesis, 2014, 12, 202-207). The advantages of this liquid support are: possibility of performing elongation reactions in the phosphoramidite or phosphotriester chemistry; stability of the matrix; presence of four anchor sites; and purifications by precipitation.

Main obstacles to the industrialization of this liquid support are the use of two hydrophobic protecting groups (in 2' and 5'), during the synthesis of RNA, and the use of non-commercial monomers and numerous purifications by precipitation.

Gallic acid derivatives, as a soluble support, were also used for the production of oligonucleotides in solution (see JP 2010-275254 and WO 2013/179412 as well as the publications of S. Kim et al, "*Liquid-Phase RNA Synthesis by Using Alkyl-Chain-Soluble Support*", Chem. Eur. J., 2013, 19, 8615-8620, and T. Shoji et al, "*Synthesis of Conjugated Oligonucleotide in Solution Phase Using Alkyl-chain-soluble Support*", Chem.—Lett. 2014, 43, 1251-1253). Using the latter, in combination with phosphoramidite chemistry, synthesis of a (21-mer) RNA was achieved in an excellent yield (26%) and good purity (78%). However, the numerous purification steps (>50) make these anchor molecules unsuitable for industrial use.

In the same vein, anchor molecules named Ajiphase™ were described for the production of oligonucleotides (see S. Katayama & K. Hirai, "*Liquid-phase synthesis of oligonucleotides*", published in S. Obika & M. Sekine (Eds.), "*Synthesis of therapeutic oligonucleotides*" (pp. 83-95), Springer Singapore, 2018). The use of Ajiphase™ as an anchor molecule for oligonucleotide production has some advantages: the anchored oligomers can be purified by simple precipitation in acetonitrile or methanol; the number of phosphoramidite equivalents is low (<2 equivalents); the overall yield is improved and the solvent consumption is reduced. However, the main limitation of this method remains purification (one precipitation per cycle).

The present invention also relates to oligosaccharides, formerly called "carbohydrates". They are involved in several biological processes and play an essential role in the living world. Indeed, sugars are involved in the structure of essential molecules such as nucleic acids (ribose and deoxyribose). Oligosaccharides and polysaccharides consist of monosaccharides linked together through a glycosidic linkage. From the perspective of understanding roles of sugars in the living world, chemists have made conceptual and practical advances that allow access to increasingly complex oligosaccharides (M. Panza et al., "*Automated Chemical Oligosaccharide Synthesis: Novel Approach to Traditional Challenges*", Chem. Rev. 2018, 118, 17, 8105-8150 and M. Guberman & P. H. Seeberger, "*Automated Glycan Assembly: A Perspective*", J. Am. Chem. Soc. 2019, 141, 14, 5581-5592).

Since Merrifield's work in the 1960's on solid support peptide synthesis, many chemists have developed similar methods, adapted to oligosaccharide synthesis, in order to benefit from advantages of this methodology, namely: the use of excess reagents and purifications by simple washing of the solid support. However, this approach to oligosaccharide synthesis involves some problems such as: choice of solid support, design of the spacer, selection of protecting groups, monitoring of reactions, choice of donor or acceptor monomers and final unhooking of the target oligosaccharide from the matrix (see P. H. Seeberger & S. J. Danishefsky, "*Solid-Phase Synthesis of Oligosaccharides and Glycoconjugates by the Glycal Assembly Method: A Five Year Retrospective*", Acc. Chem. Res. 1998, 31, 685-695; P. H. Seeberger & W.-C. Haase, "*Solid-Phase Oligosaccharide Synthesis and Combinatorial Carbohydrate Libraries*", Chem. Rev. 2000, 100, 4349-4393 and P. H. Seeberger, "*Automated oligosaccharide synthesis*", Chem. Soc. Rev. 2008, 37, 19-28).

In 1973, the first solid-state synthesis of a trisaccharide was described (see J. M. Frechet & C. Schuerch, "*Solid-Phase Synthesis of Oligosaccharides. I. Preparation of the Solid Support. Poly [p-(1-propen-3-ol-1-yl)styrene]*", J. Am. Chem. Soc. 1971, 93, 492-496; Frechet, J. M. in "*Polymer-Supported Reactions in Organic Synthesis*", Hodge, P., Sherrington, D. C., Eds.; John Wiley & Sons Ltd: Chichester, UK, 1980, pp 407-434 and Carbohydr. Res. 1972, 399-412).

Inspired by this work, Seeberger et al. designed a machine for the automated synthesis of oligosaccharides (P. H. Seeberger, "*Solid Phase Oligosaccharide Synthesis*", J. Carbohydr. Chem, 2002, 21, 613-643 and M. Weishaupt et al, "*Solid Phase Synthesis of Oligosaccharides*", published in *Methods in Enzymology,* 2010, 478, 463-484). Thus, they described the synthesis of several complex oligosaccharides such as β-glucan dodecamer derivatives.

The use of glycal for glycosidic coupling purposes has been explored on a solid support (J. T. Randolph et al, "*Major Simplifications in Oligosaccharide Synthesis Arising from a Solid-Phase Based Method: An Application to the Synthesis of the Lewis b Antigen*", J. Am. Chem. Soc. 1995, 117, 5712-5719; C. Zheng et al, "*Solid Support Oligosaccharide Synthesis: Construction of β-Linked Oligosaccharides by Coupling of Glycal Derived Thioethyl Glycosyl Donors*", J. Org. Chem, 1998, 63, 1126-1130 and K. A. Savin et al, "*A New Polymer Support Silylene Linking Method for Hindered Hydroxyl-Bearing Systems,*" J. Org. Chem. 1999, 64, 4183-4186). This concept of glycosidic coupling is based on the activation of glycal with an electrophile (dimethyldioxirane for example).

As a result of what has just been set out, main challenges for solid phase oligosaccharide synthesis are: use of excess monomer units, impossibility to control the anomericity of each monomer introduced, extrapolation to any type of glycosidic linkages, low kinetics of spacer cleavage, complex synthesis of spacers, need for special equipment (able to go down to about −20° C.) and low production capacities.

In short, the production of macromolecules, oligonucleotides and oligosaccharides, on an industrial scale at low cost and with a low environmental footprint is illusory with current methodologies. This is precisely the object of the present invention. Indeed, the inventors have developed a range of protecting groups (or anchor molecules or solubilizing molecules or anchor matrices) capable of allowing synthesis of oligonucleotides and oligosaccharides at low cost, low environmental impact and low complexity. In other words, the use of these anchor molecules allows to combine advantages of liquid phase synthesis and solid phase synthesis (homogeneity of the reaction medium, due to the fact that supports are soluble, which affords linear kinetics; the possibility to reduce the amount of expensive reagents as well as solvents; the possibility to implement large scale reactions (batch); simplified purifications of the macromolecules being elongated, of the excess reagents and of the by-products. These purifications are specifically based on the physicochemical properties and the nature of the anchor molecule, they are most often carried out by the liquid-liquid extraction technique which is based on the selective distribution (or partition coefficient or distribution coefficient) of solutes in two almost immiscible liquids.

OBJECT OF THE INVENTION

The present invention proposes to solve difficulties found in prior art, particularly with respect to the purification technique by, on the one hand, derivatizing protecting groups that could be soluble in apolar solvents and, on the other hand, using polyolefins or oligomers of polyolefins or polyalkenes, capable of causing selective solubility during the production of biological macromolecules (oligonucleotides and oligosaccharides) in liquid phase (or solution). Indeed, the inventors have found that the use of polyolefins, and in particular polyisobutene derivatives (PIB), as protecting groups or anchor molecules or liquid supports or anchor matrices, allows the synthesis of these macromolecules in solution (halogenated and/or non-halogenated solvents) while facilitating their purification by liquid-liquid extraction.

The present invention is therefore aimed at the synthesis of macromolecules by successive elongation of various units, that are mostly derivatives of carbohydrates which may be identical or different. Said macromolecules can in particular be oligonucleotides or oligosaccharides.

A first object of the present invention is a method for synthesizing macromolecules made up of units U that are mostly monosaccharides or monosaccharide derivatives, which may be identical or different, said macromolecules having a first and a second end, said synthesis method proceeding by successive elongation of said second end by a monomer or oligomer M having at least two functional groups, and said method being characterized in that:

- in a first so-called anchoring step, the first unit U1 of said macromolecule, corresponding to a monomer M1 or a terminal unit of an oligomer M1, is attached through a covalent bond (ether, ester or any other functional group compatible with the present method) to an anchor molecule soluble in organic solvents, said covalent bond resulting from a reaction of a first of the functional groups of said monomer M1 or of said oligomer M1 with a functional group of said anchor molecule, the second termination being possibly another functional group of said monomer M1 or of said oligomer M1 having been protected, prior to said reaction, by at least a first protecting group GP1, and possibly by a second protecting group GP2 and an nth protecting group GPn;

in a second so-called deprotection step, one of said protecting groups GP1 or GP2 or GPn is removed, leaving at least one free chemical functional group on said monomer M1 or said oligomer M1;

in a third so-called coupling step, a second monomer M2 or oligomer M2, carrying at least one free chemical functional group and at least one chemical functional group protected by a protecting group GP3, is reacted in such a way that its free chemical functional group forms, by reaction with said free functional group of said first monomer M1 or oligomer M1, a covalent bond, thus creating a new molecule formed by said monomer M1 or oligomer M1, attached through its first end to said anchor molecule, and said monomer M2 or oligomer M2, attached to another of its terminals, and said method being characterized in that said anchor molecule comprises a polyolefin chain or a polyolefin oligomer or a polyalkene, with at least 5 monomer units, and preferably between 10 and 50 monomer units, said polyolefin chain being a branched chain, and preferably a polyisobutene chain. Thus, an nth monomer Mn or oligomer Mn can be added by coupling; this method allows the synthesis of macromolecules.

The method comprises at least one step in which said macromolecule attached to said anchor molecule is separated from the reaction medium by the liquid-liquid extraction technique in a non-polar organic solvent with an immiscible polar solvent (or polar solvent mixture). The real challenge, therefore, is to maintain selective solubility of the anchored monomer or oligomer M1 after the deprotection and coupling reactions with respect to the by-products of said reactions.

It is the branched character of the polyolefin chain of the anchor molecule that provides it with its excellent solubility in apolar solvents and its very low solubility in polar solvents, which are necessary to allow separation of the anchor molecule from the reaction medium by liquid-liquid extraction.

The method may include a step in which said macromolecule is fully deprotected. After coupling the last monomer or oligomer, the protecting groups of the macromolecule are removed.

Said monosaccharide units or monosaccharide derivatives are, in particular, derivatives of pentoses (and in particular of nucleosides) or hexoses. Among pentoses, mention may be made, for example, of nucleosides, such as C-nucleosides, acyclic nucleosides, carboxylic nucleosides, imino-C-nucleosides, nucleosides with modified bases; all these molecules have to be used in a suitably protected form. Other usable monosaccharide derivatives are osamines (amino sugars), such as glucosamine, galactosamine, mannosamine, meglumine.

The linkage between two successive units is an osidic (and preferably glycosidic) or phosphorylated (especially ose-1-phosphate) or carbohydrate or N-heteroside or S-heteroside linkage.

In one embodiment of the method, some of the units U may not be monosaccharides or monosaccharide derivatives. In particular, such units U may be selected from amino acids and lipids (isoprene derivatives).

Said anchor molecule advantageously has a mass average molecular mass between 300 and 20,000, and preferably between 500 and 15,000. Its polyolefin chain is an oligomer or a polymer built from monomers that are preferably identical.

In one advantageous embodiment, said polyolefin chain or polyolefin or polyalkene oligomer has been obtained by polymerization of a monomer. This monomer is advantageously biosourced.

In one particular embodiment, said polyolefin or polyalkene oligomer chain comprises a number of unsaturated carbon-carbon bonds not exceeding 5%, and preferably not exceeding 3%.

A second object of the invention is the use of a method according to any one of the embodiments of the invention for the synthesis of oligonucleotides or oligosaccharides.

In the case of oligonucleotides, the monomeric unit typically consists of a suitably protected phosphorylated nucleoside (or oligonucleotide chain) (Scheme 1). This unit will react with the alcohol in the 5' position of a suitably protected nucleoside (or oligonucleotide chain) on the nucleic base and/or in the 2' position of the sugar and anchored in the 3' position to a liquid support.

Scheme 1

[Chem 1]

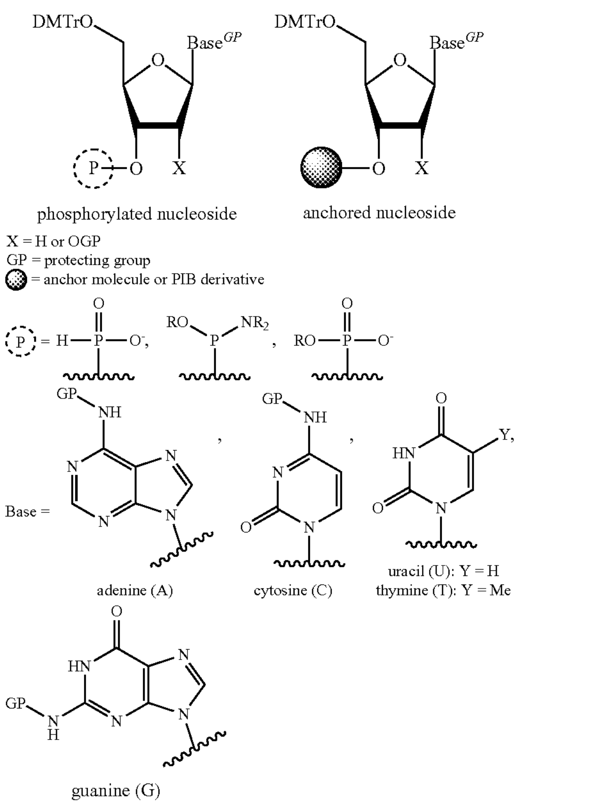

In the case of oligosaccharides, the monomeric unit typically consists of a suitably protected or unprotected donor glycosyl (or oligosaccharide chain) carrying a Z group, in the anomeric position, which may be but is not limited to a cyclic hemiacetal, acetate, thioglycoside, phosphate or imidate. The alcohol functionality of a suitably protected or unprotected acceptor glycoside (or oligosaccharide chain) anchored to a liquid support will react with said monomeric unit (Scheme 2).

Scheme 2

[Chem 2]

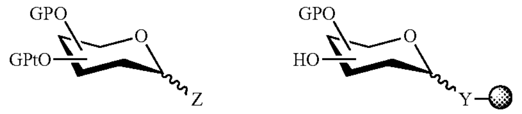

Z = imidate, phosphate, thioglycoside...
GPt = temporary protecting group
Y = O, S, NH-NH
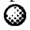 = anchor molecule or PIB derivative Generally speaking, the method according to the invention can be carried out with identical or different units. By way of example, an oligosaccharide can thus be synthesized which is a homopolymer, namely which consists of identical monosaccharide units. An oligosaccharide can also be synthesized from different monosaccharide units. Units that are disaccharides, trisaccharides or longer oligosaccharides can also be used. Similarly, oligonucleotides can be synthesized from identical or different phosphorylated nucleoside (or oligonucleotides) units.

By way of example, to prepare oligonucleotides, nucleosides 3' (2-cyanoethyl-N,N-dialkylphosphoramidite) or nucleosides 3'-(H-phosphonates) or nucleoside phosphates (di or triesters), can be used. In the synthesis of oligosaccharides, suitably protected or unprotected donor glycosyls can be used. In both cases, coupling reactions known to the skilled person are applied.

The method according to the invention also allows the synthesis of mixed polysaccharides comprising monosaccharide units and nucleotide units.

The method according to the invention also makes it possible to introduce, into the macromolecule, units which are or comprise neither oligosaccharides nor oligonucleotides.

One essential characteristic of the method according to the invention is the use of anchor molecules or solubilizing molecules or anchor matrices. They have to be soluble in an apolar solvent. They consist of a polyolefin chain having at least 5 monomer units, and preferably between 10 and 50 units; they are polyolefins or oligomers of polyolefins or polyalkenes. Advantageously, the anchor molecules are functionalized at at least one of their ends to allow protection or attachment of the initial monomer (or oligomer) unit.

Said anchor molecule may comprise in each of its units identical or non-identical alkyl groups, which are preferably selected from the group consisting of methyl and ethyl. Said polyolefin chain advantageously has a mass average molecular mass of between 300 and 20,000, and preferably between 500 and 15,000. Said polyolefin chain may comprise a number of unsaturated carbon-carbon bonds not exceeding 5%, and preferably not exceeding 3%. Preferably it is a polyisobutene (abbreviated as PIB) chain. Scheme 3 shows some PIBs usable within the scope of the invention; in these formulae, X represents a spacer that carries the functional group intended to react with the first unit U1 of the macromolecule to achieve anchoring to the liquid support.

Scheme 3

[Chem 3]

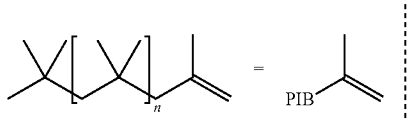

n = 10 to 50

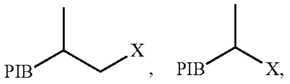

X = spacer
Functionalized PIB

The method according to the invention allows access to high purity macromolecules. This method induces an advantageous E-factor (environmental factor) because the purifications are performed by the liquid-liquid extraction technique, with reasonable quantities of solvent, which allows to minimize the purification steps by chromatography columns; generating, consequently, financial savings. Thus, reactions for derivatizing by-products soluble in apolar solvents can be performed before the liquid-liquid extraction.

In one particular embodiment, said anchor molecule comprises a polyolefin chain (or is a polyolefin chain) terminated by at least one group selected from the group (spacer) consisting of an aliphatic chain (branched or unbranched and unsaturated or not), a (hetero) ring and/or a (hetero) aryl (substituted or not).

In one advantageous embodiment, the mass average molecular mass of the anchor molecules, excluding their terminal functionalization, is between 300 and 20,000, and preferably between 500 and 15,000. Beyond a mass average molecular mass of about 20,000, these molecules may exhibit excessive viscosity, which would limit their solubility in organic solvents.

Some PIB derivatives used in the scope of the present invention are commercially available as ligands for homogeneous catalysis. By way of example, 2-methyl-3-[polyisobutyl(12)]propanol (mass average molecular mass 757, including terminal functionalization) or 4-[polyisobutyl(18)]phenol (mass average molecular mass 1104, including terminal functionalization) which are distributed, respectively, under the reference numbers 06-1037 and 06-1048 by the company Strem Chemicals can be used. These two molecules are derivatives of polyisobutene whose chain is terminated, respectively, by a $—CH_2—C(CH_3)(H)—CH_2—OH$ group (i.e. isopropanol) and by a $—CH_2—C(CH_3)_2—C_6H_4—OH$ group (i.e. phenol).

According to one characteristic of the invention, the anchor molecules act as protecting groups, alcohol functional groups and/or any other functional groups that need to be inert under the conditions of the method that is the subject of the present invention.

In the case of oligonucleotide synthesis, the alcohol functionality in the 3'-position of the ribose/deoxyribose and/or an amine of the nucleobase can be masked, simultaneously or not, with at least one solubilizing protecting group.

In the case of oligosaccharide synthesis, the initial anomeric functional group is anchored (protected) with a solubilizing protecting group.

These derivatizations allow solubilization of monomers and oligomers in apolar solvents such as cyclohexane, heptane(s) or hexane(s).

According to another characteristic of the invention, the use of anchor molecules soluble in organic solvents as described above (and more particularly the use of polyolefins), and insoluble in some polar solvents (such as water and/or ethanol and/or acetonitrile), facilitates purification of the anchored monomers and oligomers by simple liquid-liquid extraction or simple filtration on silica.

According to yet another characteristic of the invention, commercially available anchor molecules, or anchor molecules that can be synthesized in a simple and direct manner from commercially available precursors, including some polyisobutene derivatives, are used. In other words, conventional protecting groups can be linked to the PIB, such as benzyl, silyl or carboxylic acid derivatives.

FIG. 4 below sets forth some not exhaustive structures, capable of playing the role of a protecting group in the synthesis of oligonucleotides.

Scheme 4

[Chem 4]

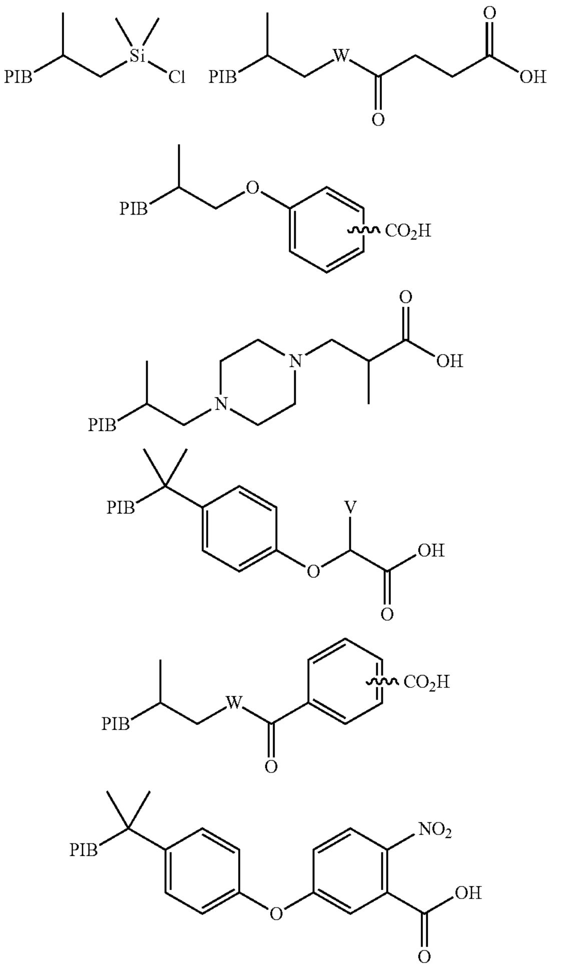

-continued

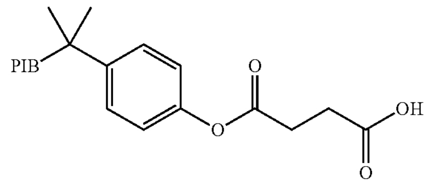

V = H or Me
W = O, NH, $NHR^5$, piperazine
$R^5$ = alkyl, (hetero)aryl

Scheme 5 below sets forth some not exhaustive structures capable of playing the role of protecting group in the synthesis of oligosaccharides.

Scheme 5

[Chem 5]

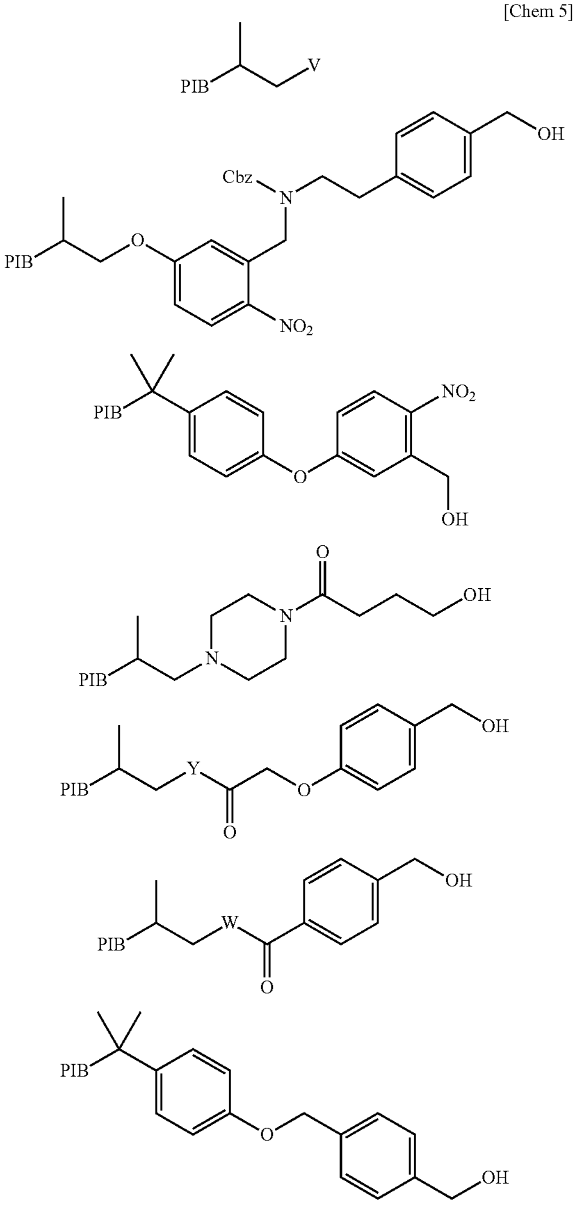

-continued

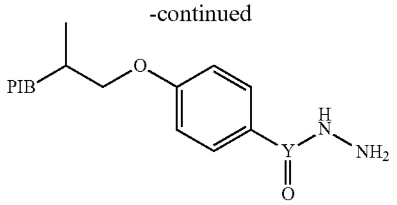

V = OH or $Si(Me)_2Cl$
W = O, NH, $NHR^5$, piperazine
$R^5$ = alkyl, (hetero)aryl
Y = C or SO According to yet another characteristic of the invention, the initial monomer (or oligomer) is attached to the anchor molecule according to known reactions depending on the chemical functional groups in an appropriate solvent, such as (halogenated or non-halogenated) solvent mixtures, and at a temperature between −50° C. and 150° C.

According to yet another characteristic of the invention, chemical functional groups of the monomer (or oligomer), which are incompatible with this method, can be temporarily masked by appropriate protecting groups such as tert-butyldimethylsilyl (abbreviated as TBDMS or TBS), dimethoxytrityl (abbreviated as DMTr) or any other protecting group compatible with the present method.

According to yet another characteristic of the invention, after the deprotection step, the protecting groups can be derivatized, preferably in situ, to form compounds soluble in a polar solvent (or polar solvent mixture). Thus, the monomer (or oligomer) anchored to a PIB derivative whose primary alcohol is protected by a trityl group is cleaved in an acidic medium in the presence of a corresponding carbocation (trityl) scavenger to make it soluble in the aqueous (or polar) phase. Trityl carbocation scavengers include, but are not limited to, thioglycolic acid, 3-mercaptoproprionic acid, 3-mercapto-1-propanesulfonic acid, cysteine or thiomalic acid (or mercaptosuccinic acid).

According to yet another characteristic of the invention, said anchor molecule reacts with a suitably protected first monomer (or oligomer), leading to a covalent bond, such as an ester or O-glycoside bond, between these two molecular species.

According to yet another characteristic of the invention, monomers having chemical functional groups incompatible with the reaction conditions of the elongation (or iteration) cycle can be temporarily masked by a solubilizing protecting group. In this case, depending on the length of the target macromolecule, chemical functional groups can be masked by one or more solubilizing protecting groups and by one or more conventional protecting groups such as: benzoyl, acetyl, tert-butyldimethylsilyl.

According to yet another characteristic of the invention, the macromolecule synthesis method is performed using monomer units (or oligomers) linked to an anchor molecule as a starting point.

In the case of oligonucleotide synthesis, the first elongation cycle starts with a selective deprotection of the 5' protecting group of the anchored nucleoside in acidic medium and in the presence of a scavenger, if it is a trityl derivative.

In the case of oligosaccharide synthesis, the first elongation cycle starts with a reaction between a suitably protected or unprotected donor glycosyl and a glycoside anchored and deprotected on the alcohol functionality that will be involved in the reaction. Again, if the protecting group is a trityl derivative, it is deprotected in acidic medium in the presence of a scavenger.

According to yet another characteristic of the invention, the integration of a unit (or iteration) of monomer requires several steps.

In the case of oligonucleotide synthesis, two steps are necessary for nucleoside phosphates (coupling and deprotection of the alcohol in the 5' position), and three steps for nucleoside phosphoramidites or H-phosphonates (coupling, oxidation and deprotection of the alcohol in the 5' position).

In the case of oligosaccharide synthesis, two steps are necessary (coupling and deprotection).

According to yet another characteristic of the invention, said macromolecule is formed by n monomer units with a chemical functional group bonded to an anchor molecule. During the course of the method, the oligomer chain grows by successive elongation (or cycling) or iteration, and during each of these steps a monomer or oligomer unit is added, at the free alcohol end.

According to yet another characteristic of the invention, natural and/or unnatural and/or synthetic monomers (or oligomers) can be used in said oligomer chain.

According to yet another characteristic of the invention, one or more suitably protected monomer (or oligomer) analog units such as morpholino phosphorus monomers or N-acetyl monosaccharide monomers may be used in said oligomer chain.

According to yet another characteristic of the invention, at least one step in which said oligomer chain is purified from the reaction medium by extraction in a water-immiscible apolar organic solvent (or immiscible with a water/ethanol mixture or a water/acetonitrile mixture) or by filtration on silica. As apolar organic solvent, hydrocarbons only containing carbon and hydrogen atoms are preferred, such as linear alkanes, branched alkanes and cycloalkanes, and cyclohexane, heptanes and hexanes are particularly preferred.

According to yet another characteristic of the invention, the method makes it possible to obtain high purity oligomers, after total deprotection and un-anchoring of the anchor molecules, for their intended use, for example as active principle for preclinical trials, clinical care or any other applications.

According to yet another characteristic of the invention, the anchor molecules can be reused (recycled) in the method according to the invention.

According to yet another characteristic of the invention, the extraction solvents can be reused (recycled) in the method according to the invention.

The method according to the invention can be automated and/or performed in flow chemistry.

DETAILED DESCRIPTION

In the present invention, the terms below are used with the following meaning, which is in accordance with the terminology of the International Union of Pure and Applied Chemistry (IUPAC), and any other terms used should also be understood as defined by IUPAC.

The term "carbohydrate" comprises monosaccharides, oligosaccharides and polysaccharides as well as compounds derived from monosaccharides by reduction of the carbonyl functionality (especially the aldehyde or ketone functionality), by oxidation of at least one functional group at the end of the chain to a carboxylic acid, or by replacement of one or more hydroxyl groups with a hydrogen atom, an amino group, a thiol group or with any similar atom. This term also includes derivatives of such compounds.

The term "monosaccharide" refers to the monomer of carbohydrates.

The term "glycosylamine" means a compound in which a carbohydrate is linked to an amine group in an anomeric position.

The term "nucleoside" refers to a ribosyl or deoxyribosyl derivative of some pyrimidine or purine bases, more precisely glycosylamines consisting of a nucleobase linked to the anomeric carbon atom of a pentose residue, generally ribose (ribonucleoside) or deoxyribose (deoxyribonucleoside), by a glycosidic linkage from the $N^1$ atom of a pyrimidine or the $N^9$ atom of a purine.

The term "nucleotide" refers to an organic molecule that is the building block of a nucleic acid such as DNA or RNA; this molecule is made up of a nucleic base, a five-carbon ose, and finally one to three phosphate groups.

The term "protecting group" refers to a molecule used for reversible protection of a functional group during a chemical reaction to make said functional group non-reactive in said chemical reaction process which would have transformed said unprotected functional group.

The term "functional group" means an atom or group of atoms that can react with other functional groups. Examples of functional groups are the following: aldehyde, carboxylic acid, phosphoric acid, phosphonic acid, sulfonic acid, primary or secondary amine, ketone, alkyl halide, hydrazine, hydroxylamine, hydroxyl, isocyanate, isothiocyanate, thiol.

The term "macromolecule" refers to a high molecular mass molecule designed from a succession of low molecular mass units. These units can be linked individually and successively to form a chain; an oligomer comprising several of these units can also be coupled. Generally speaking, these units can be identical or different. The macromolecules can be of synthetic or biological origin or a combination of both. They may comprise one or more functional groups. The term "macromolecule" as used herein includes polymers; in the case of a polymer, said unit is called a monomer.

The term "polymer" refers to a macromolecule comprising repeating structural units, namely monomers, connected by chemical bonds in a linear, circular, branched, cross-linked, dendrimeric manner or a combination thereof. It is understood that a polymer may, for example, also comprise at least one functional group. A polymer is called a "homopolymer" if the polymer is made up of the same monomers and is called a "copolymer" if the polymer is made up of different monomers.

According to one characteristic of the invention, which will be described in greater detail below, the anchor molecules or solubilizing protecting groups or anchor matrix are polyolefins, or more precisely polyolefin oligomers (polyolefins being also called polyalkenes) and derivatives thereof, that is they carry at least one functional group.

In one preferred embodiment, the method according to the invention uses polyolefins, or more precisely oligomers of polyolefins (polyolefins being also called polyalkenes), and their derivatives as anchor molecule or protecting group or anchor matrix, of several functional groups of various monomers, at least monofunctional, linked by a covalent bond (ester, amide, ether, thioether or any other suitable chemical functional groups), making the new monomeric derivative soluble in apolar liquid phase. Polyolefin molecules comprise a chain of carbon atoms linked by single bonds. They may include branches consisting of identical or different, but preferably identical, alkyl groups. Preferably, the polymers consist of a number of monomer units of at least 10 and preferably between 15 and 50. Homopolymers are preferred, but copolymers (saturated or unsaturated) can be used. In the case of unsaturated polymers or copolymers, the number of unsaturated bonds in the chain of carbon atoms advantageously does not exceed 5%, and preferably does not exceed 3%.

In one preferred embodiment, these are derivatives of polyisobutenes (PIBs), a class of polymers known since the 1930s, but derivatives of polypropylenes can also be used.

These anchor molecules employed in the method according to the invention are preferably in the form of functionalized derivatives. The preceding Schemes 4 and 5 show a number of PIB derivatives with their functionalizations that are suitable for carrying out the present invention.

According to one characteristic of the invention, these anchor molecules are linked to a monomer (or oligomer) unit, by a covalent bond such as amide, ether, thioether, thioester ester, sulfonylhydrazide or acylhydrazide (non-exhaustive list). This assumes that the PIB derivatives involved are suitably functionalized. This functionalization of the anchor molecules is as a general rule in the terminal position, namely preferably at one of the ends of the carbon atom chain.

According to the invention, the multifunctional monomers (or oligomers) can be functionalized with PIB derivatives via a covalent bond, in the form of ester, ether, thioether, thioester or any other chemical functionalities compatible with the present method. This acts as a solubilizing protecting group for the monomers (or oligomers).

Polyolefin oligomers used as anchor molecules are typically characterized by a mass average molecular mass, but "pure" oligomers that have identical molecules of a given chain length can also be used.

The reaction between the anchor molecule and the monomer (or oligomer) leads to a new molecule with a low water solubility (<30 mg/mL).

According to another characteristic of the invention, PIB functionalization, by chemical reactions, leads to various molecular structures, capable of acting as solubilizing protecting groups, of an at least bifunctional molecule (or intermediate) of interest, during a multi-step synthesis. It is implied that the protecting group is also at least monofunctional. Otherwise, the chemical functional group not involved in the linkage between the PIB derivative and the molecule (or intermediate) of interest have to be inert or suitably protected, to avoid any spurious products or side reactions.

According to another characteristic of the invention, chemical functional groups of the monomer (or oligomer) not involved in the covalent bond with the PIB derivative, directly or not, have to be passive or suitably protected, to avoid formation of undesirable products.

In a further aspect of the invention, the molecule resulting from the reaction between the PIB derivative and a monomer (or oligomer), via the formation of a covalent bond, directly or not, is characterized in that it has a low solubility in water (<30 mg/mL). Stated differently, the PIB derivative acts as a solubilizing molecule.

According to another characteristic of the invention, the molecule resulting from the reaction between the PIB derivative and a monomer (or oligomer), via the formation of a covalent bond, directly or not, is characterized in that the PIB derivative significantly increases the solubility of the monomer (or oligomer) in apolar solvents (cyclohexane, heptane(s), hexane(s) or aromatic solvents) or any other suitable solvent. Thus, the new monomeric (or oligomeric) derivative has a selective solubility (a high partition coefficient) for an apolar solvent during a liquid-liquid extraction (in the presence of water or a water/ethanol or water/acetonitrile mixture), making the purification method simple, fast and cheap.

The protection reaction between the PIB derivative and a monomer (or oligomer), via the formation of a covalent bond, directly or indirectly (spacer), is carried out in any solvent or inert liquid that can dissolve the reactants, at an appropriate temperature. Applicable solvents, pure or as mixtures, include, but are not limited to, halogenated or non-halogenated hydrocarbons. Preferred solvents are dichloromethane and toluene (alone or in the presence of N—N-dimethylformamide).

Depending on the free chemical functional groups of the monomer (or oligomer) and the anchor molecule, various chemical reactions are possible. The formation of the new monomer or oligomer derivative can therefore be carried out according to all methods known to the skilled person. By way of non-exhaustive examples, applicable reactions include esterification reactions, amidation reactions or etherification reactions. Consequently, the reaction conditions (solvent(s), temperature(s), concentration(s), duration(s)) have to be adapted for each protection reaction.

Depending on the chemical nature of the bond between the monomer (or oligomer) and the anchor molecule, the deprotection steps can be carried out using reaction conditions known to the person skilled in the art. Without being exhaustive, saponification, hydrolysis and hydrogenolysis can be mentioned. More precisely, the method for solubilizing a suitably protected and anchored monomer (or oligomer) via a covalent bond according to the invention is characterized in that it is solubilized in an organic solvent. Stated differently, the anchor molecule acts as a solubilizing molecule and a protecting group of a chemical functional group of the monomer (or oligomer).

The monomer (or oligomer), suitably protected and covalently bound to an anchor molecule (of various kinds), is characterized in that its solubility in water is low (<30 mg/mL). Stated differently, the anchor matrix acts as a solubilizing entity. This derivatization significantly increases the solubility of the new molecule to the point that it becomes soluble in apolar organic solvents. Consequently, monomers (or oligomers) anchored to a PIB derivative have a high partition coefficient (selective solubility (or selective distribution)) for the apolar organic phase during a liquid-liquid extraction in the presence of cyclohexane or heptane(s) or hexane(s) and water or a water/ethanol or water/acetonitrile mixture, allowing a simple and fast purification.

The present invention opens the possibility of convergent synthesis of long oligomers, which can be achieved by using at least two suitably protected oligomer fragments, at least one of which is bound to an anchor molecule.

Reaction scheme 6 below shows a complete sequence for producing an oligonucleotide. More precisely, in a first so-called anchoring step, a first monomer unit (in this case a deoxyribose derivative) protected by a protecting group (in this case DMTr) is attached to a liquid support molecule according to the invention; the product obtained is purified by liquid-liquid extraction. In a second so-called deprotection step, the protecting group (DMTr) is removed and scavenged in an acidic medium in the presence of a scavenger and the product obtained is purified by liquid-liquid extraction. It is preferable to perform anchoring and deprotection (with scavenging) without isolation of the intermediate protected alcohol.

Scheme 6: Synthesis of oligonucleotides.

[Chem 6]

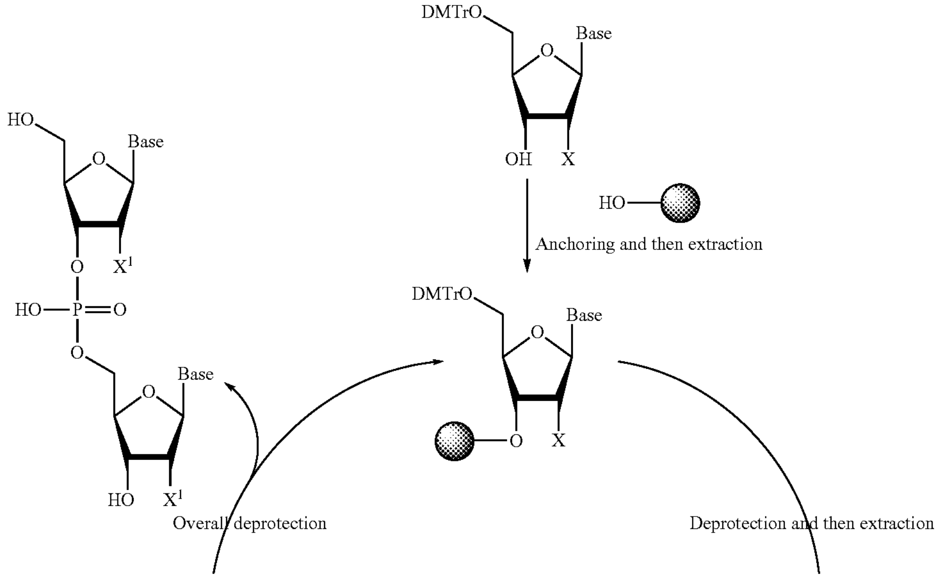

-continued

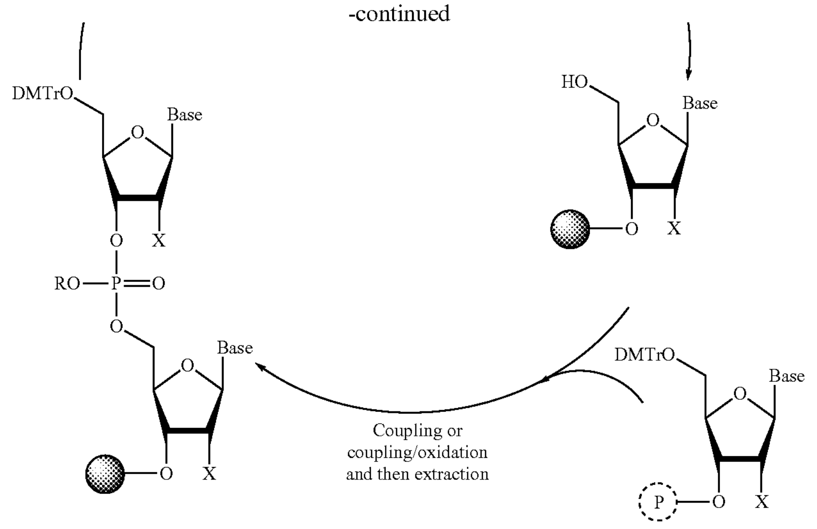

X = H, OTBS, OTOM
$X^1$ = H, OH
R = cyanoethyl or aromatic

After the deprotection step, the protecting groups can be derivatized, preferably in situ, to form compounds soluble in a polar solvent (or mixture thereof). Thus, the monomer (or oligomer) anchored to a PIB derivative whose primary alcohol is protected by a trityl group is cleaved in an acidic medium in the presence of a scavenger of the corresponding carbocation (trityl) for making it soluble in the aqueous (or polar) phase. Scavengers for the trityl carbocation can advantageously be selected from the group consisting of: thioglycolic acid, 3-mercaptoproprionic acid, 3-mercapto-1-propanesulfonic acid, cysteine, thiomalic acid, mercaptosuccinic acid. An example of this deprotection is represented in Scheme 7 below.

Scheme 7: Deprotection of a DMTr protecting group

[Chem 7]

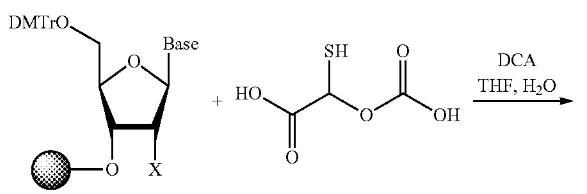

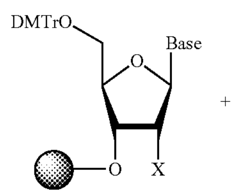

-continued

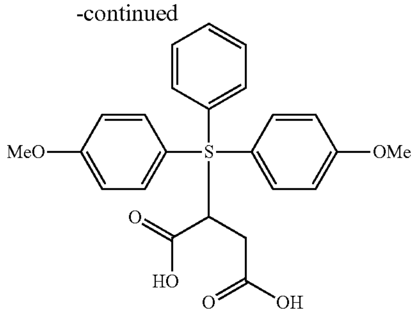

Soluble in polar solvents
(water, water/ethanol or water/acetonitrile)

In a third so-called coupling/oxidation (sulfurization) step, a second monomer unit (in this case a phosphorylated ribose derivative) protected by a protecting group (in this case DMTr) is introduced. In the case of phosphoramidite chemistry, the coupling reaction is carried out in the presence of tetrazole or any other appropriate reagents (benzylthio-1H-tetrazole (BTT), 4,5-dicyanoimidazole), followed by an oxidation reaction (metachloroperbenzoic acid (mCPBA), iodine, 2-butanone peroxide). A dinucleotide is thus obtained; the reagents and side products are separated by extraction.

In a fourth step called general deprotection, this dinucleotide, which is still bound to the liquid support molecule according to the invention, can be deprotected and then detached from this support. Alternatively, it can enter a new cycle for the addition of a third unit, and so on.

Reaction scheme 8 below shows a complete sequence for producing an oligosaccharide. More precisely, in a first so-called anchoring step, a first monomer unit (in this case a hexose derivative) protected or not by a first, stronger protecting group (GP) and by a second, more labile protective or not protecting group, called temporary (GPt) is attached to a liquid support molecule on the anomeric position according to the invention; this compound is purified by extraction. In a second so-called selective deprotection step, said second protecting group (GPt) is removed, and the compound is purified by extraction. In a third so-called glycosylation step, a second monomer unit (in this case a protected or unprotected donor glycosyl derivative) is added and coupled to said first unit to form an anchored disaccharide; the reactants and by-products are removed by liquid-liquid extraction. In a fourth so-called overall deprotection step, this disaccharide is deprotected and then separated from the liquid support. Alternatively, it can enter a new cycle, after selective deprotection of a functional group, if necessary, to initiate a new cycle, and so on.

content", as well as in ISO 16620-2:2015 "Plastics-Biobased Content-Part 2: Determination of Biobased Carbon Content" and ISO 16620-3:2015 "Plastics-Biosourced Content-Part 3: Determination of Biobased Synthetic Polymer Content", for methods of determining and quantifying biosourced nature.

Advantageously, anchor molecules used in the present invention have a biosourced carbon content greater than 90%, preferably greater than 93%, and even more preferably greater than 95%.

Scheme 8: Synthesis of oligosaccharides.

[Chem 8]

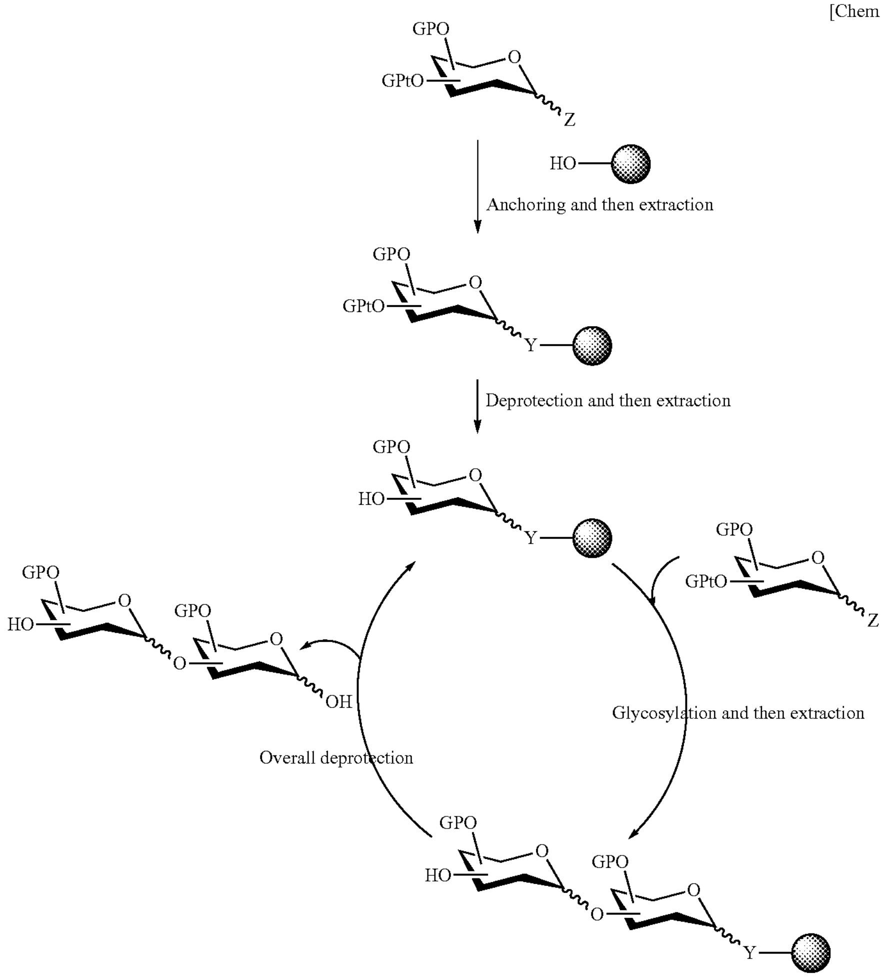

Among anchor molecules, those that are able to be manufactured by a polymerization technique from simple monomers are preferred. This is the case of polyisobutenes (PIBs), which represent one particularly preferred type of anchor molecules. The monomer of polyisobutenes, namely isobutene, can be industrially manufactured from biosourced feedstocks, and PIBs can be prepared from the biosourced isobutene by simple polymerization. Thus, the present invention can be implemented with biosourced anchor molecules, and in particular with biosourced PIB.

The concept of biosourced content is defined in ISO 16620-1:2015 "Plastics-Biosourced Content-Part 1: General Principles", including a definition of the terms "biosourced synthetic polymer", "biosourced synthetic polymer content", "biosourced carbon content" and "biosourced mass The method according to the invention has many advantages.

A first advantage is that it allows to obtain matrix-bound oligomers with good purity by simple liquid-liquid extraction in an apolar organic solvent and water or a water/ethanol or water/acetonitrile mixture or by filtration on silica, causing the removal of by-products (salts, excess reagents or any other molecular species) that are not bound to the polyolefin or polyalkene oligomer derivatives. Apolar organic solvents such as cyclohexane, heptane(s), hexane(s) which have flash points <15° C., are appropriate for solubilizing the polyolefin or polyolefin oligomer or polyalkene derivatives during extraction or washing. The method according to the invention thus facilitates purification steps and produces less waste (effluents and stationary phase).

A second, particularly interesting, advantage is the possibility of automating the method according to the invention.

A third advantage is the possibility to recycle extraction solvents as well as anchor molecules (polyolefins or oligomers of polyolefins or polyalkenes), especially on an industrial scale. Indeed, these protecting groups can be easily removed at the end of the synthesis by reactions usually used in organic synthesis (such as hydrolysis, saponification, hydrogenolysis or any other reaction compatible with the present method) and recycled. This proves that the method according to the invention is in line with green or sustainable chemistry, contrary to current production methods.

A fourth advantage of the invention lies in the possibility of accessing large oligomers, either by modulating the size of the anchor molecule, or by moving towards convergent synthesis, or by introducing one or more anchor molecules onto monomeric units.

A fifth advantage is the possibility to control the purity of the oligomer during the synthesis, at each step by different analytical techniques such as mass spectrometry, high performance liquid chromatography, proton or carbon-13 nuclear magnetic resonance.

A sixth advantage is the possibility to implement, on an industrial scale, without expensive equipment.

Thanks to their high purity, macromolecules produced by this method can be used as pharmaceuticals, cosmetics, phytosanitary products or agri-food products, or to access any of these products.

Yet another advantage is that the preferred anchor molecules, namely polyisobutene derivatives, can be prepared from biosourced isobutene, as explained above.

EXAMPLES

The following examples illustrate the synthesis of some functionalized anchor molecules that can be used to implement the method according to the invention.

Unless otherwise indicated, known PIB derivatives have been prepared from precursors and methods described (Tetrahedron, 2005, 61, 12081) and commercial reagents.

Example 1: General O-Arylation Procedure

[Chem 9]

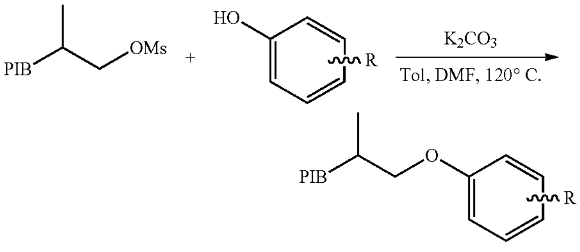

To a mixture of PIB—$CH_2$—$CH(CH_3)$—$CH_2$-OMs derivative (1 equivalent) and phenol (3 equivalents) in a toluene/N—N-dimethylformamide (1/1) (0.1 M) mixture, potassium carbonate (5 equivalents) has been added, and then the reaction medium has been heated at 120° C. for 16 h and then cooled to room temperature. The reaction medium has been extracted three times with cyclohexane and acetonitrile/water or ethanol/water (90/10) mixture, washed with brine, dried over sodium sulfate, filtered, concentrated under reduced pressure and the residue purified by silica filtration, if necessary, to yield the corresponding O-aryl derivative.

Example 2

[Chem 10]

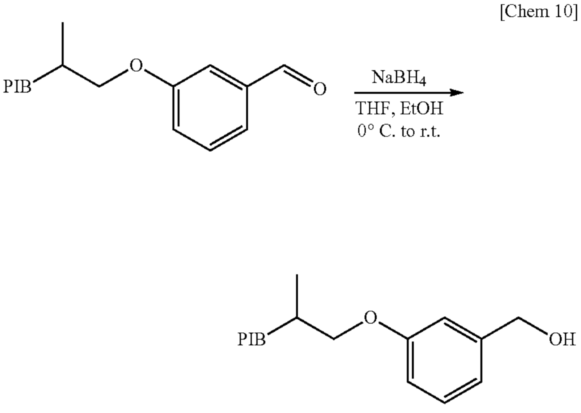

The anchored aldehyde (1 equivalent), has been dissolved in a (0.1 M) tetrahydrofuran/ethanol (1/1) mixture, and then cooled to 0° C. for 5 minutes. Sodium borohydride (3 equivalents) has been added to the reaction medium (in small portions), and then the reaction medium has been stirred at room temperature for 30 minutes. The reaction medium has been concentrated under reduced pressure, and then 1N sodium hydroxide solution and cyclohexane have been successively added to the residue. The organic phase has then been washed with water, brine, dried over sodium sulfate, filtered and concentrated under reduced pressure to yield the corresponding benzyl alcohol.

Example 3

[Chem 11]

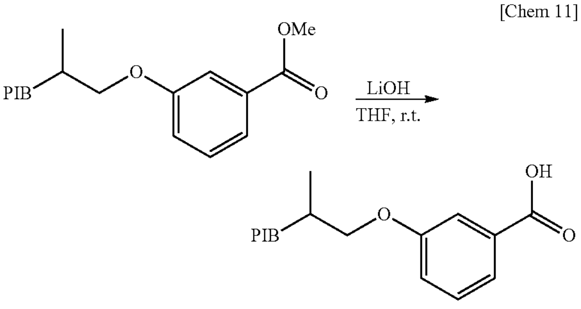

The anchored methyl ester (1 equivalent) has been dissolved in a (0.1 M) tetrahydrofuran/DMSO/water (8/1/1) mixture. Lithium hydroxide (3 equivalents) has been added to the reaction medium, and then the reaction medium has been stirred at room temperature for 12 h. The reaction medium has been extracted three times with cyclohexane and washed successively with hydrochloric acid solution (1N), ethanol/water mixture (90/10), brine, dried over sodium sulfate, filtered, concentrated under reduced pressure and the residue has been purified by silica filtration, if necessary, to yield the corresponding carboxylic acid.

Example 4

[Chem 12]

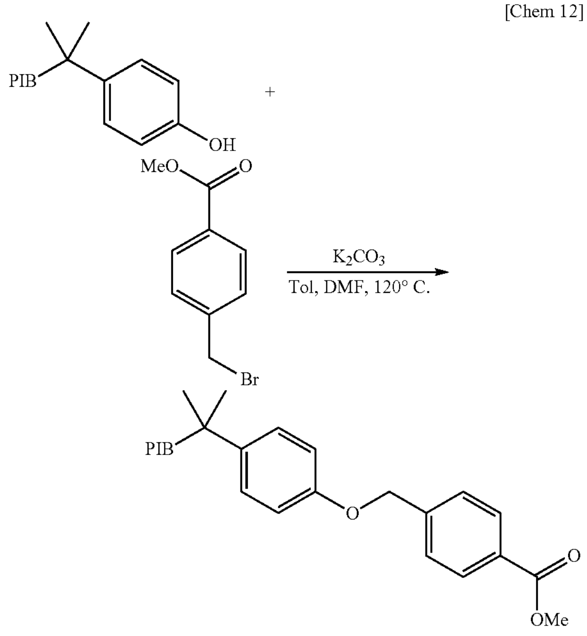

To a mixture of PIB-phenol derivative (1 equivalent) and methyl 4-(bromomethyl)benzoate (3 equivalents) in a (0.1 M) toluene/N—N-dimethylformamide (1/1) mixture has been added potassium carbonate (5 equivalents) then the reaction medium has been heated at 120° C. for 16 h then cooled to room temperature. The reaction medium has been extracted three times with cyclohexane and washed successively with an acetonitrile/water or ethanol/water (90/10) mixture, brine, dried over sodium sulfate, filtered, concentrated under reduced pressure, and the residue is purified by filtration on silica, if necessary, to yield the corresponding O-aryl derivative.

Example 5

[Chem 13]

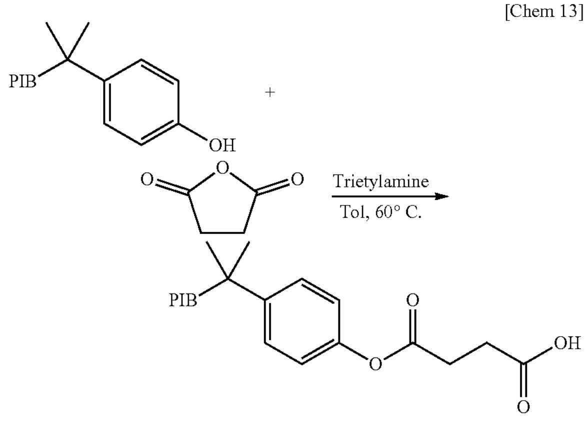

To a solution of the PIB-phenol derivative (1 equivalent) in toluene (0.1 M), under stirring and at room temperature, succinic anhydride (2 equivalents), and then triethylamine (3 equivalents) have been added. The reaction medium has been heated to 60° C. for 16 h and then cooled to room temperature. After addition of a (1N) hydrochloric acid solution, the reaction medium has been extracted three times with cyclohexane and the organic phase has been washed successively with an ethanol/water (90/10) mixture, brine, dried on sodium sulfate, filtered, concentrated under reduced pressure and the residue has been purified by filtration on silica, if necessary, to yield the corresponding ester.

Example 6

[Chem 14]

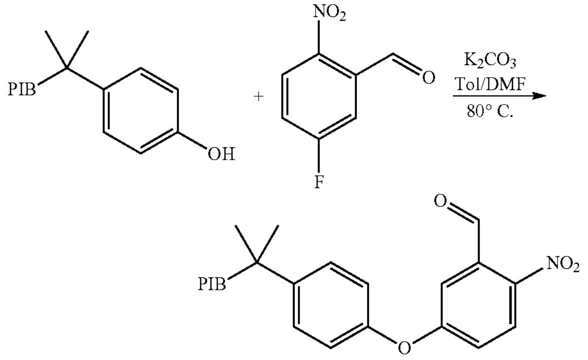

To a solution of the PIB-phenol derivative (1 equivalent) in toluene/DMF (1/1) (0.1 M), under stirring and at room temperature, 5-fluoro-2-nitrobenzaldehyde (3 equivalents), and then potassium carbonate (3 equivalents) have been added. The reaction medium has been heated to 80° C. for 48 h and then cooled to room temperature. The reaction medium has been extracted three times with cyclohexane and washed with an ethanol/water (90/10) mixture, brine, dried over sodium sulfate, filtered, concentrated under reduced pressure and the residue is purified by silica filtration, if necessary, to yield the corresponding aryl ether.

Example 7

{Chem 15]

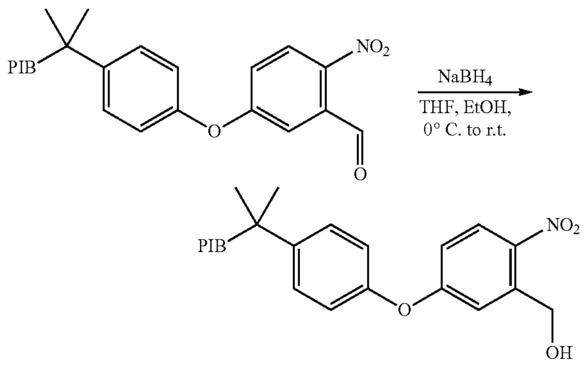

The anchored aldehyde (1 equivalent) has been dissolved in a (0.1 M) tetrahydrofuran/ethanol (1/1) mixture, and then cooled to 0° C. for 5 minutes. Sodium borohydride (3 equivalents) has been added to the reaction medium (in small portions) and then the reaction medium has been stirred at room temperature for 30 minutes. The reaction medium has been concentrated under reduced pressure, and then 1N sodium hydroxide solution and cyclohexane have been successively added to the residue. The organic phase has then been washed with water, brine, dried over sodium sulfate, filtered and concentrated under reduced pressure to yield the corresponding benzyl alcohol.

Example 8

[Chem 16]

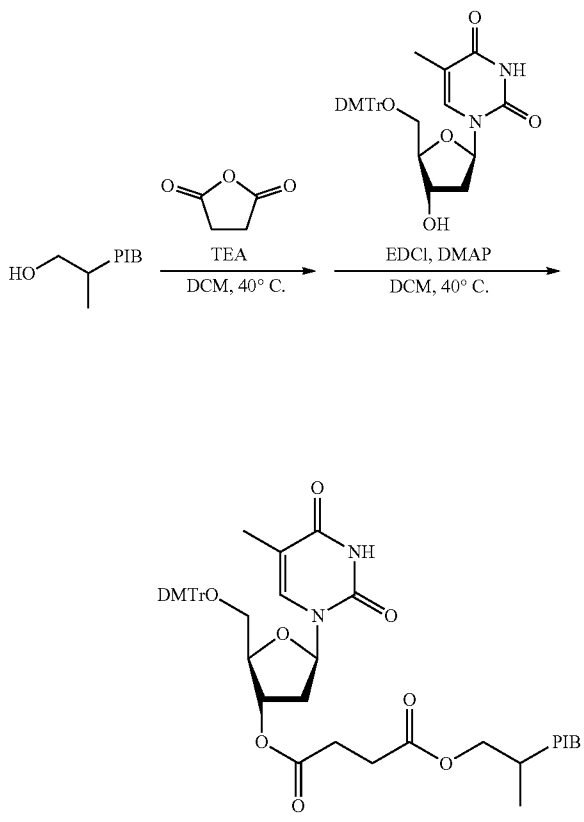

To a solution of the PIB-alcohol derivative (1 equivalent) in dichloromethane (0.1 M) under stirring, under an inert atmosphere and at room temperature, succinic anhydride (1.1 equivalent), and then triethylamine (1.2 equivalent) have been added. The reaction medium has been heated to 40° C. for 18 h and then cooled to room temperature.

At this stage, 5'-O-(4,4'-dimethoxytrityl)thymidine (1.1 equivalent), ethyl-(N,N-dimethylamino)-propylcarbodiimide hydrochloride (EDCI) (1.1 equivalent) and 4-(N,N-dimethylamino)-pyridine (DMAP) (0.5 equivalent) have been successively added to the reaction medium; then the reaction medium has been heated at 40° C. for 18 h. The reaction medium has been evaporated and then extracted with cyclohexane, washed 3 times with an ethanol/water (90/10) mixture, brine, dried over sodium sulfate, filtered, concentrated under reduced pressure and the residue has been purified by silica filtration, if necessary, to yield the corresponding anchored thymidine.

Example 9

[Chem 17]

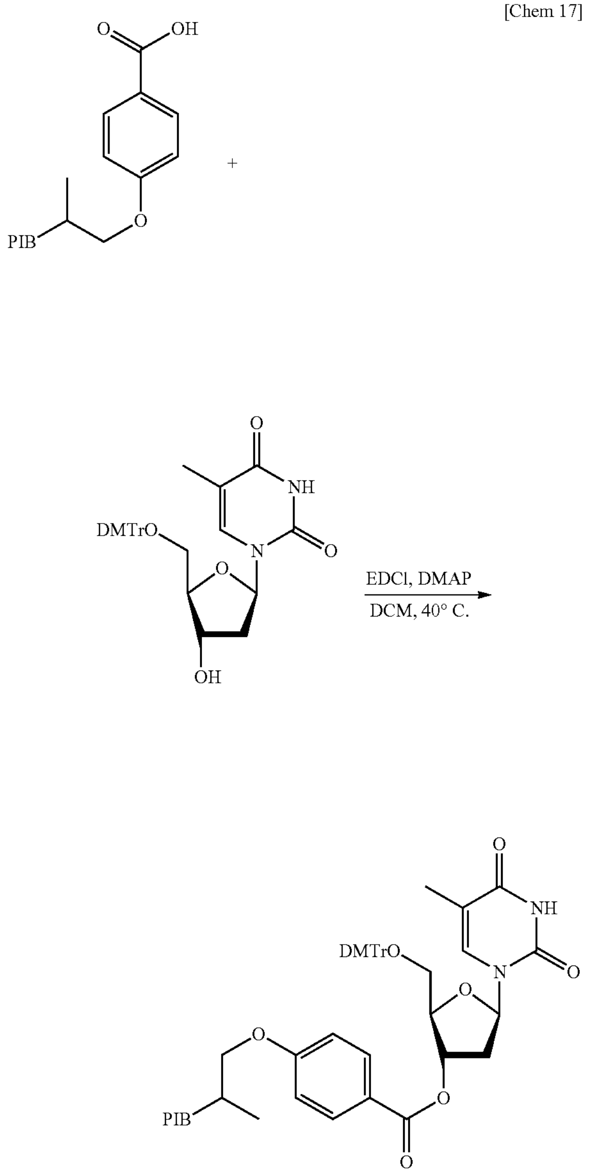

To a solution of the PIB-carboxylic acid derivative (1 equivalent) in dichloromethane under stirring, inert atmosphere and at room temperature 5'-O-(4,4'-dimethoxytrityl) thymidine (1.1 equivalent), ethyl-(N,N-dimethylamino)-propylcarbo-diimide hydrochloride (EDCI) (1.1 equivalent) and 4-(N,N-dimethylamino)-pyridine (DMAP) (0.5 equivalent) have been added, and then the reaction medium has been heated to 40° C. for 18 h. The reaction medium has been evaporated and then extracted with cyclohexane, washed 3 times with an ethanol/water (90/10) mixture, brine, dried over sodium sulfate, filtered, concentrated under reduced pressure and the residue has been purified by silica filtration, if necessary, to yield the corresponding anchored thymidine.

Example 10

[Chem 18]

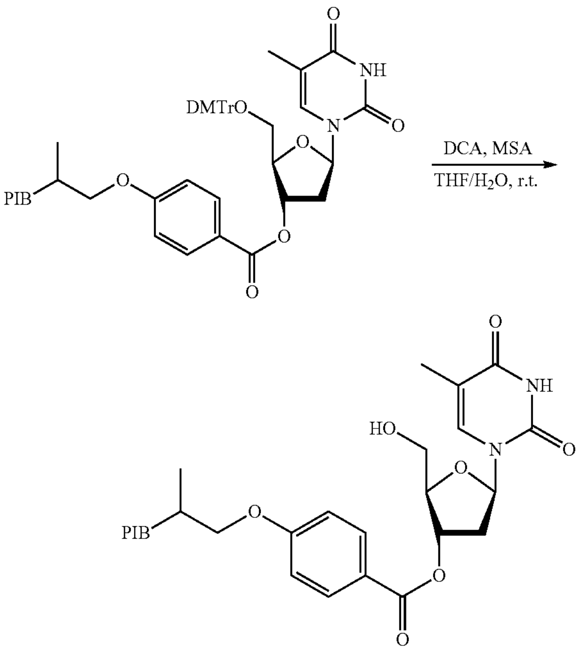

To a solution of the anchored 5'-O-(4,4'-dimethoxytrityl) thymidine derivative (1 equivalent) in a (0.1 M) THF/$H_2O$ mixture, at room temperature, mercaptosuccinic acid (5 equivalents) then dichloroacetic acid (5% V) have been added, and then the reaction medium has been stirred for 1 h. The reaction medium has been evaporated, and then extracted with cyclohexane, washed 3 times with ethanol/water mixture (90/10), brine, dried on sodium sulfate, filtered, concentrated under reduced pressure to yield the deprotected derivative of corresponding anchored thymidine.

Example 11

[Chem 19]

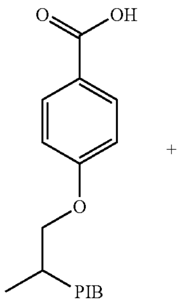

-continued

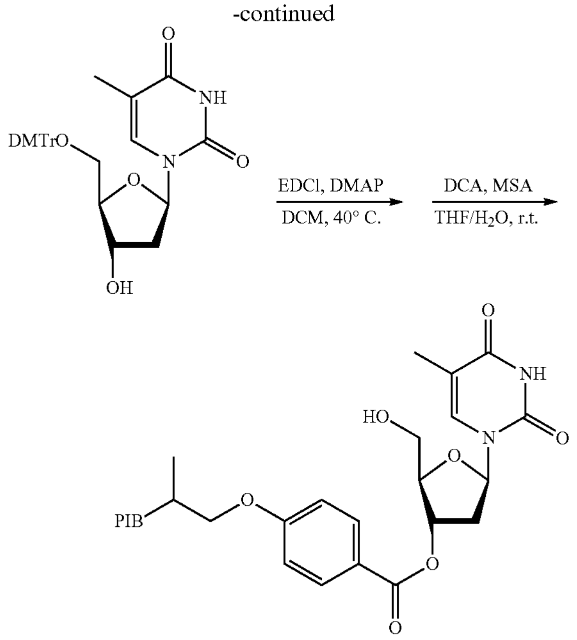

To a solution of the PIB-carboxylic acid derivative (1 equivalent) in dichloromethane (0.1 M) under stirring in an inert atmosphere and at room temperature, 5'-O-(4,4'-dimethoxytrityl)thymidine (1.1 equivalent), ethyl-(N,N-dimethylamino)-propylcarbodiimide hydrochloride (EDCI) (1.1 equivalent) and 4-(N,N-dimethylamino)-pyridine (DMAP) (0.5 equivalent) have been added. Then the reaction medium has been heated at 45° C. for 18 h and then evaporated.

The residue has been solubilized in a (0.1 M) THF/$H_2O$ (9/1) mixture, at room temperature, and then mercaptosuccinic acid (5 equivalents), dichloroacetic acid (5% V) have been successively added then the reaction medium has been stirred at room temperature for 1 h. The reaction medium has been evaporated, and then extracted with cyclohexane, washed 3 times with an ethanol/water (90/10) mixture, a saturated sodium bicarbonate solution, brine, dried over sodium sulfate, filtered, concentrated under reduced pressure to yield the deprotected derivative of the corresponding anchored thymidine.

Example 12

[Chem 20]

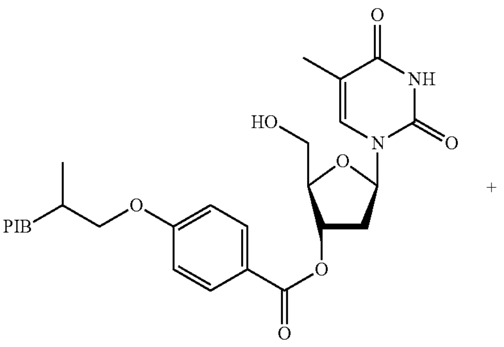

-continued

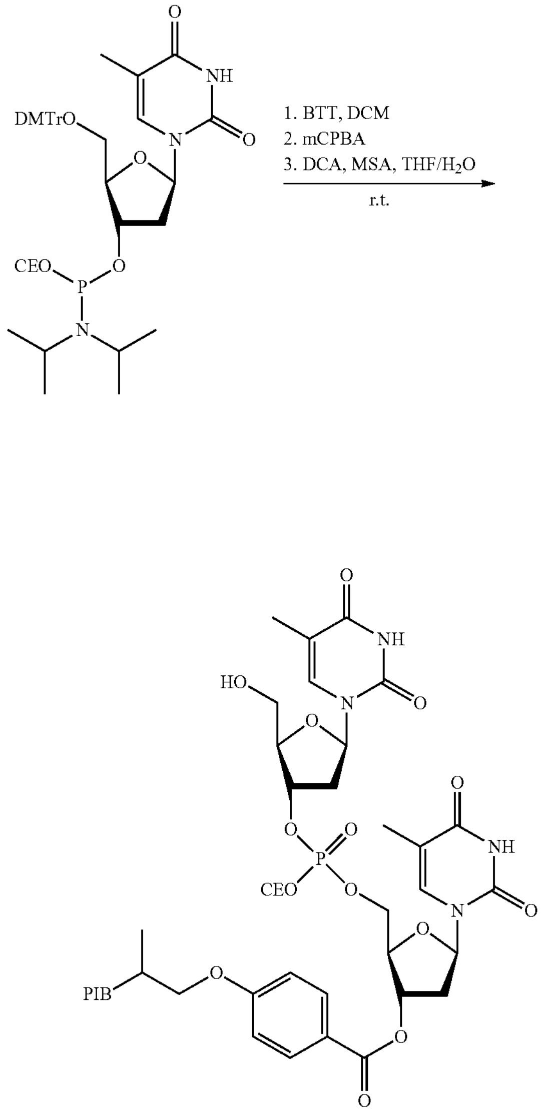

The deprotected derivative of the anchored thymidine (1 equivalent) and DMT-dT phosphoramidite (2 equivalents) have been co-evaporated 3 times with anhydrous toluene and then dried under vacuum. To the residue under inert atmosphere dichloromethane (0.1 M) then a benzylthio-1H-tetrazole (BTT) solution (4.5 equivalents) in (0.01 M) acetonitrile have been added and the reaction medium has been stirred for 16 h at room temperature. mCPBA (3 equivalents) has been added to the reaction medium then stirred for 1 h and then evaporated.

At this stage, the residue has been solubilized in a (0.1 M) THF/$H_2O$ (9/1) mixture, at room temperature, then mercaptosuccinic acid (5 equivalents), dichloroacetic acid (5% V) have been successively added, and then the reaction medium has been stirred at room temperature for 1 h. The reaction medium has been evaporated, and then extracted with cyclohexane, washed 3 times with an ethanol/water (90/10) mixture, an aqueous sodium bicarbonate solution (10%), brine, dried over sodium sulfate, filtered, concentrated under reduced pressure to yield the dimeric deprotected derivative of the corresponding anchored thymidine.

Example 13

[Chem 21]

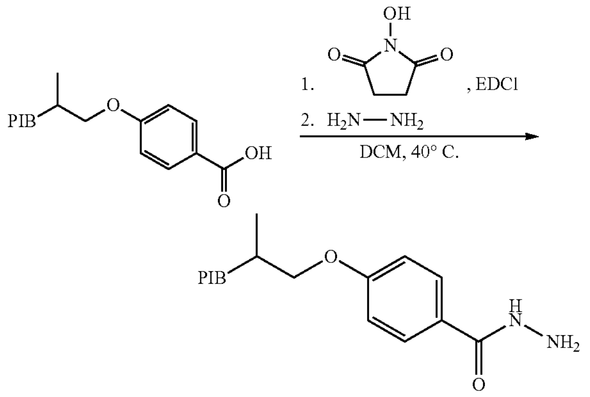

To a solution of the PIB-benzoic acid derivative (1 equivalent) in dichloromethane (0.1 M) under stirring, under an inert atmosphere and at room temperature, N-hydroxysuccinimide (1.1 equivalent), ethyl-(N,N-dimethylamino)-propylcarbodiimide hydrochloride (EDCI) (1.1 equivalent) and 4-(N,N-dimethylamino)-pyridine (DMAP) (0.1 equivalent) have been added, and then the reaction medium has been heated to 40° C. for 30 min and then cooled to room temperature. Hydrazine hydrate has been added to the reaction medium and then heated to 40° C. for 30 min. The reaction medium has been evaporated, and then extracted with cyclohexane, washed 3 times with an ethanol/water (90/10) mixture, brine, dried over sodium sulfate, filtered, concentrated under reduced pressure to yield the corresponding PIB-acyl hydrazide derivative.

Example 14

[Chem 22]

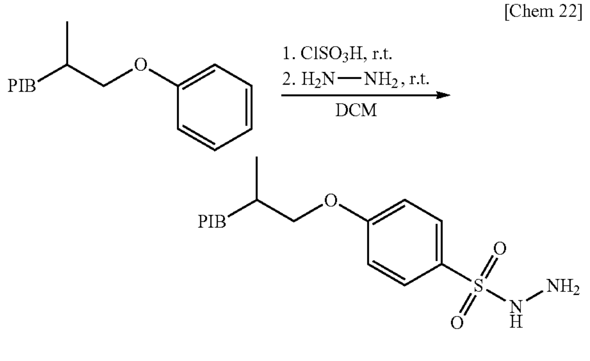

To a solution of the PIB-aryl derivative (1 equivalent) in dichloromethane (0.1 M) under stirring, under an inert atmosphere and at room temperature, chlorosulfuric acid (1.1 equivalent) has been added dropwise, then the reaction medium has been stirred at room temperature for 30 min. Hydrazine hydrate (3 equivalents) has been added to the reaction medium and then stirred for 30 min. The reaction medium has been evaporated, and then extracted with cyclohexane, washed 3 times with an ethanol/water (90/10) mixture, brine, dried over sodium sulfate, filtered, concentrated under reduced pressure to yield the corresponding PIB-sulfonyl hydrazide derivative.

Example 15

[Chem 23]

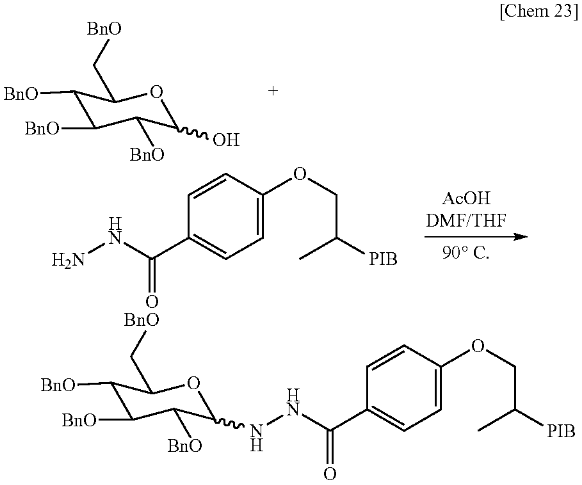

To the PIB-acyl hydrazide (1 equivalent) and 2,3,4,6-tetra-O-benzyl-D-glucopyranose (1.5 equivalent) mixture in a (0.1 M) DMF/THF (9/1) mixture, acetic acid (0.01 equivalent) has been added and then the reaction mixture has been heated to 90° C. for 18 h. The reaction medium has been evaporated and then extracted with cyclohexane, washed 3 times with ethanol/water mixture (90/10), brine, dried over sodium sulfate, filtered, concentrated under reduced pressure to yield the corresponding PIB-glycosylhydrazide derivative.

Example 16

[Chem 24]

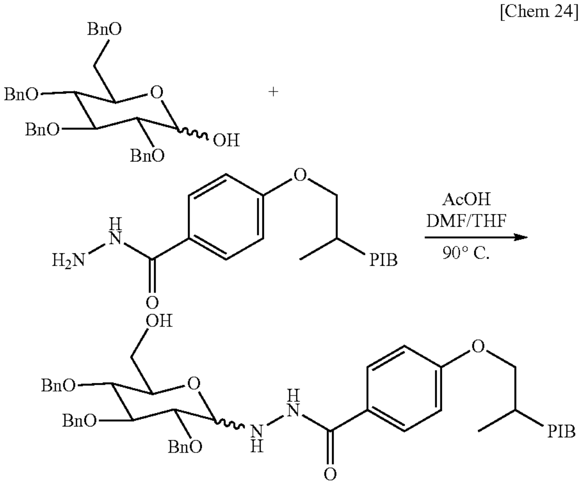

To the PIB-acyl hydrazide (1 equivalent) and 2,3,4,-tri-O-benzyl-D-glucopyranose (1.5 equivalent) mixture in a (0.1 M) DMF/THF (9/1) mixture, acetic acid (0.01 equivalent) has been added, and then the reaction mixture has been heated at 90° C. for 18 h. The reaction medium has been evaporated, and then extracted with cyclohexane, washed 3 times with an ethanol/water (90/10) mixture, brine, dried over sodium sulfate, filtered, concentrated under reduced pressure to yield the corresponding PIB-glycosylhydrazide derivative.

The invention claimed is:

1. A method for synthesizing macromolecules made up of units U that are mostly monosaccharides or monosaccharide derivatives, which may be identical or different, said macromolecules having a first and a second end, said synthesis method proceeding by successive elongation of said second end by a monomer or oligomer M having at least two functional groups, and said method being characterized in that:

in a first anchoring step, the first unit U1 of said macromolecule, corresponding to a monomer M1 or a terminal unit of an oligomer M1, is attached by a covalent bond to an anchor molecule soluble in non-polar organic solvents, said covalent bond resulting from a reaction of a first of the functional groups of said monomer M1 or of said oligomer M1 with a functional group of said anchor molecule, the second termination possibly being another functional group of said monomer M1 or of said oligomer M1 that has been protected, prior to said reaction, by at least a first protecting group GP1, and possibly by a second protecting group GP2;

in a second deprotection step, one of said protecting groups GP1 or GP2 is removed, leaving a free functional group on said monomer M1 or oligomer M1;

in a third coupling step, a second monomer M2 or oligomer M2, carrying at least one free functional group and at least one functional group protected by a protecting group GP3, is reacted so that its free functional group forms, by reaction with said free functional group of said first monomer M1 or oligomer M1, a covalent bond, thus creating a new molecule formed by said monomer M1 or oligomer M1, attached by its first end to said anchor molecule, and said monomer M2 or oligomer M2, attached to another of its terminations, and said method being characterized in that said anchor molecule comprises a polyisobutene chain with at least 5 monomer units.

2. The method according to claim 1, characterized in that an n-th monomer Mn or oligomer Mn is added by coupling.

3. The method according to claim 2, characterized in that after coupling the last monomer or oligomer, deprotection of the protecting groups of the macromolecule is carried out.

4. The method according to claim 3, comprising at least one step in which said macromolecule attached to said anchor molecule is separated from the reaction medium by extraction in an apolar organic solvent, and/or by extraction or washing with a polar solvent, and/or by filtration.

5. The method according to claim 4, comprising a step in which said macromolecule is fully deprotected.

6. The method according to claim 5, characterized in that said monosaccharide units or monosaccharide derivatives are pentose or hexose derivatives.

7. The method of claim 6, wherein the pentose derivative is in a nucleoside.

8. The method according to claim 6, characterized in that the bond between two successive units is a bond of the osidic type or of the carbohydrate type or of the N-heteroside type or of the S-heteroside type.

9. The method of claim 8, wherein the osidic type is a glycosidic type or a phosphorylated type.

10. The method of claim 9, wherein the phosphorylated type is an ose-1-phosphate type.

11. The method of claim 8, wherein the osidic type is an ose 1 phosphate type.

12. The method according to claim 8, characterized in that said anchor molecule has a mass average molecular mass between 300 and 20,000.

13. The method of claim 12, wherein the mass average molecular mass is between 500 and 15,000.

14. The method according to claim 12, characterized in that said polyolefin or polyolefin oligomer or polyalkene chain comprises a number of unsaturated carbon-carbon bonds not exceeding 5%.

15. The method of claim 14, wherein the number of unsaturated carbon-carbon bonds does not exceed 3%.

16. The method according to claim 14, characterized in that said polyisobutene chain has been obtained by polymerization of a biosourced monomer.

17. The method according to claim 16, wherein the method is used for synthesizing oligonucleotides or oligosaccharides.

18. The method according to claim 1, wherein said anchor molecule comprises between 10 and 50 monomer units.

* * * * *